United States Patent [19]

Era et al.

[11] Patent Number: 4,935,125
[45] Date of Patent: Jun. 19, 1990

[54] DIALYSIS SYSTEM

[75] Inventors: Kazuo Era, 1-18-33, Sakae-Machi, Tachikawa-Shi, Tokyo; Mitsutaka Ueda; Yoshihiko Sano, both of Osaka; Tateki Takakuwa; Inobu Fujikawa, both of Kanazawa, all of Japan

[73] Assignees: Shibuya Kogyo Co., Ltd., Ishikawa; Nissho Corporation, Osaka; Kazuo Era, Tokyo, all of Japan

[21] Appl. No.: 237,496

[22] Filed: Aug. 26, 1988

[30] Foreign Application Priority Data

Sep. 1, 1987 [JP] Japan ................................. 62-218722
Sep. 1, 1987 [JP] Japan ................................. 62-218723
Apr. 30, 1988 [JP] Japan ................................. 63-108787

[51] Int. Cl.$^5$ ............................................. B01D 13/00
[52] U.S. Cl. .................................... 210/101; 210/103; 210/143; 210/206; 210/257.2; 210/295; 210/321.65; 210/321.71; 210/929
[58] Field of Search ................. 210/101, 103, 94, 143, 210/195.2, 206, 257.2, 295, 321.65, 321.71, 929; 137/98.99, 100

[56] References Cited

U.S. PATENT DOCUMENTS

| | | | |
|---|---|---|---|
| 3,493,495 | 2/1970 | Mendelson | 210/321.75 |
| 3,498,910 | 3/1970 | Mendelson | 210/321.72 |
| 4,037,616 | 7/1977 | Pinkerton | 210/321.71 |
| 4,209,391 | 6/1980 | Lipps | 210/321.65 |
| 4,366,061 | 12/1982 | Papanek et al. | 210/929 |
| 4,477,342 | 10/1984 | Allan et al. | 210/321.71 |
| 4,676,905 | 6/1987 | Nagao et al. | 210/321.65 |
| 4,698,160 | 10/1987 | Haraguchi | 210/321.71 |

FOREIGN PATENT DOCUMENTS 5682 1/1981 Japan.

Primary Examiner—W. Gary Jones
Attorney, Agent, or Firm—Flynn, Thiel, Boutell & Tanis

[57] ABSTRACT

A dialysis system operates to supply dialysate to a dialyzer from a feed chamber in response to a reduction in the volume of the feed chamber, and to recover used dialysate which is flowed out from the dialyzer into a recovery chamber in response to an increase in the volume of the recovery chamber. The increase in the volume of the recovery chamber is greater in magnitude than the magnitude of a reduction in the volume of the feed chamber, with a difference therebetween being effective to control the amount of ultrafiltration. At least two sets of feed chambers and recovery chambers may be provided, and a supply of the dialysate from the other feed chamber may be initiated before the supply from one of the feed chambers is completed, thus allowing the dialysate to be continuously supplied to the dialyzer.

14 Claims, 4 Drawing Sheets

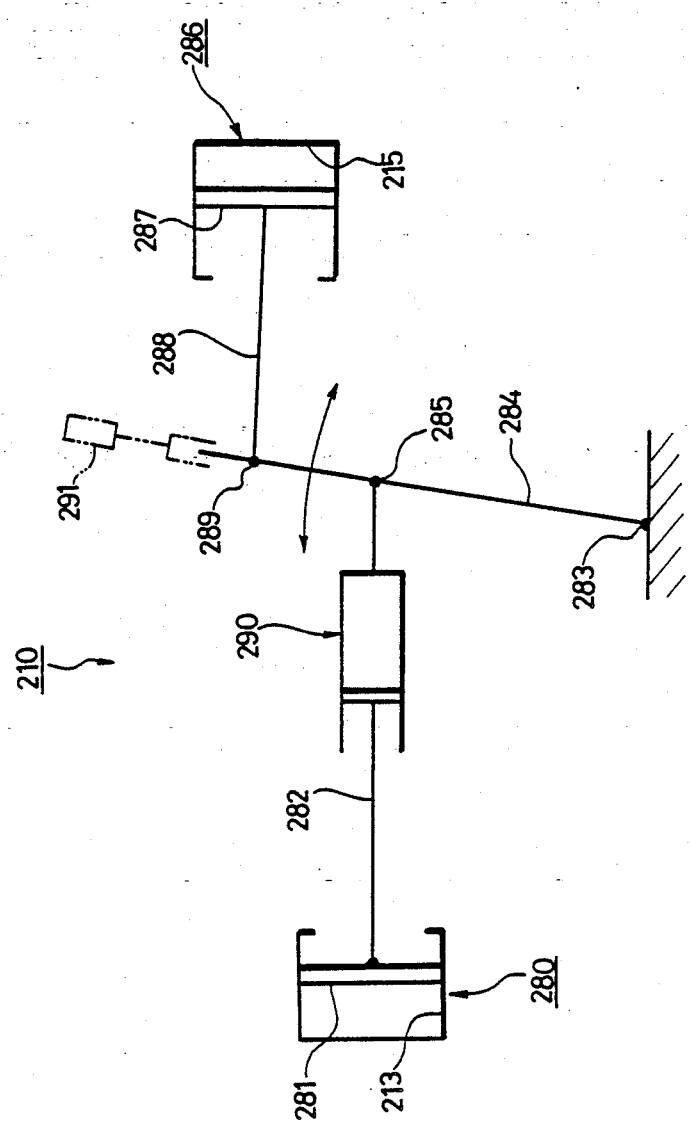

DIALYSIS SYSTEM

FIELD OF THE INVENTION

The invention relates to a dialysis system which removes wastes or water content from blood.

DESCRIPTION OF THE PRIOR ART

A dialysis system is known in which a dialysate container is divided into a feed chamber and a recovery chamber by a movable diaphragm, and the feed chamber is connected to an inlet and the other chamber or recovery chamber is connected to an outlet of a dialyzer so that a first closed line is defined by the feed chamber, the dialyzer and the recovery chamber, and a second closed line which is constructed in the same manner as the first closed line is connected to the dialyzer so that the both closed lines may be alternately switched for connection to the dialyzer (see Japanese Patent Publication No. 82/1981).

In each closed line, a fresh dialysate introduced into the feed chamber is supplied to the dialyzer in response to a reduction in the volume thereof which occurs as the movable diaphragm moves while simultaneously receiving used dialysate which is flowed out from the dialyzer into the recovery chamber in response to an increase in the volume thereof which occurs as the movable diaphragm moves.

In a dialysis system constructed in the manner mentioned above, the first closed line is connected to the dialyzer while the second closed line is disconnected therefrom, and a fresh dialysate introduced into the feed chamber of the first line is supplied to the dializer in response to a reduction in the volume thereof which occurs as the movable diaphragm moves while simultaneously recovering used dialysate which is flowed out from the dialyzer into the recovery chamber in response to an increase in the volume thereof which occurs as the movable diaphragm moves. During the time the fresh dialysate is being supplied to the dialyzer through the first line, a fresh dialysate is introduced into the feed closed chamber of the second closed line while a used dialysate is simultaneously drained out externally from the recovery chamber.

Upon termination of the supply of the fresh dialysate from the first line, this line is disconnected from the dialyzer while simultaneously connecting the second closed line to the dialyzer for initiation of the supply of a fresh dialysate therefrom, thus alternately supplying the fresh dialysate to the dialyzer.

In a dialysis system of the type described, in each closed line, the amount of fresh dialysate which is supplied from the feed chamber to the dialyzer can be brought an accurate coincidence with the amount of used dialysate which is recovered from the dialyzer into the recovery chamber. Accordingly, an amount of used dialysate which is removed from part of the closed line will be in an accurate coincidence with an amount of ultrafiltration, and hence the amount of ultrafiltration can be accurately controlled in terms of an amount of used dialysate which is removed out of the closed line.

However, in order to perform the dialysis, it is necessary that a greater amount of used dialysate be flowed out from the dialyzer than the amount of fresh dialysate which is supplied to the dialyzer from the feed chamber. In the dialysis system of the type mentioned above, the amount of fresh dialysate which is supplied from the feed chamber to the dialyzer coincides with the amount of used dialysate which is recovered from the dialyzer into the recovery chamber, and hence there is a need to provide means, which is effective to remove an amount of used dialysate corresponding to the amount of ultrafiltration, located intermediately the closed line. A high reliability and durability are required of such means in order to maintain a constant amount of ultrafiltration per unit time over a long time. In the prior art approach, the amount of ultrafiltration is determined by metering the dialysate which is removed, and accordingly, the metering means may be subject to contamination by the dialysate, disadvantageously causing an error in the quantity being metered.

It will be noted that in a dialysis system of the type described, because the first and the second closed line are alternately connected to the dialyzer in a switching manner, the supply of a fresh dialysate to the dialyzer ceases during the switching, disadvantageously increasing a length of time required for the dialysis.

A fresh dialysate normally comprises a mixture of dilution water, a concentrated liquid containing calcium ions, magnesium ions, and so on, and a concentrated liquid containing bicarbonate in a given proportion. A different kind of fresh dialysate is also known which comprises dilution water and a concentrated liquid containing acetate mixed together in a given proportion. Before the fresh dialysate is introduced into the feed chamber, the concentrated liquid and dilution water are mixed in a given proportion by a mixer, which then supplies the mixture to the feed chamber. However, the mixer is provided with a mixing tank to which the concentrated liquid and dilution water are supplied at a given rate, and because a relatively increased amount of fresh dialysate is prepared in one step within the mixing tank, there is a disadvantage that the mixer of an increased size requires an additional space therefor.

SUMMARY OF THE INVENTION

In view of the foregoing, the invention provides an improvement in a dialysis system of the type described in which a feed chamber including a movable diaphragm is connected to an inlet while a recovery chamber including a movable diaphragm is connected to an outlet of the dialyzer so that the feed chamber, the dialyzer and the recovery chamber form together a closed line, with a fresh dialysate introduced into the feed chamber being supplied to the dialyzer in response to a reduction in the volume of the feed chamber while simultaneously recovering used dialysate which is flowed out from the dialyzer into the recovery chamber in response to an increase in the volume thereof. The improvement comprises separate movable diaphragms which are used to partition the feed and the recovery chamber, respectively, and which are coupled together through interlock means which causes the volume of the recovery chamber to increase or decrease as the volume of the feed chamber decrease or increase, respectively. The interlock means is associated with means which enables a free control of a difference between a variation in the volume of the recovery chamber and a variation in the volume of the feed chamber.

With this arrangement, a difference between a variation in the volume of the recovery chamber and a variation in the volume of the feed chamber can be made to coincide with an amount of ultrafiltration, thus dispensing with means of the prior art, which was disposed intermediately in a closed line to remove used dialysate.

This facilitates securing a high level of reliability and durability in comparison to the provision of such means. Since the amount of ultrafiltration can be controlled in accordance with the magnitude of a difference between variations of the volumes, a more positive control over the amount of ultrafiltration can be exercised than when used dialysate is directly removed from the closed line.

In accordance with another aspect of the invention, a dialysis system includes a feed line which feeds fresh dialysate to the feed chamber. The feed line comprises a supply of concentrated liquid which is connected to at least the feed chamber through a first open/close valve, and a supply of dilution water which is connected to the feed chamber through a second open/close valve. Whenever fresh dialysate is to be fed into the feed chamber, the movable diaphragm associated with the feed chamber is moved in a direction to increase the volume thereof, and the first and the second open/close valve are opened in an alternate fashion so that the concentrated liquid and the dilution water are sequentially introduced into the feed chamber in given increments, thereby allowing a fresh dialysate to be prepared within the feed chamber through a mixing process.

With this arrangement, the first and the second open/close valves are alternately opened to allow the concentrated liquid and the dilution water to be sequentially introduced into the feed chamber in given increments, allowing a fresh dialysate to be prepared by mixture within the feed chamber, thus eliminating the need for the provision of a separate mixing tank as required in the prior art and thus allowing a reduction in the size of the entire system.

In accordance with a further aspect of the invention, the dialysis system including at least two closed lines of the kind described above is operated in a manner such that before a feed passage and a recovery passage of the first closed line which is then connected to the dialyzer are closed, a feed passage and a recovery passage of the other closed line are opened in an overlapped manner or while the feed passage and the recovery passage of the first closed line remain open. By repeating such operation, it is possible to maintain a continuous supply of fresh dialysate to the dialyzer. In this manner, an interruption in the supply of fresh dialysate to the dialyzer is avoided, enabling a loss in time to be eliminated.

Above and other objects, features and advantages of the invention will become apparent from the following description of several embodiments thereof with reference to the drawings.

BRIEF DESCRIPTION OF THE DRAWINGS

FIG. 4 is a schematic illustration of a further embodiment of the invention.

DETAILED DESCRIPTION OF EMBODIMENTS

Figure 1:
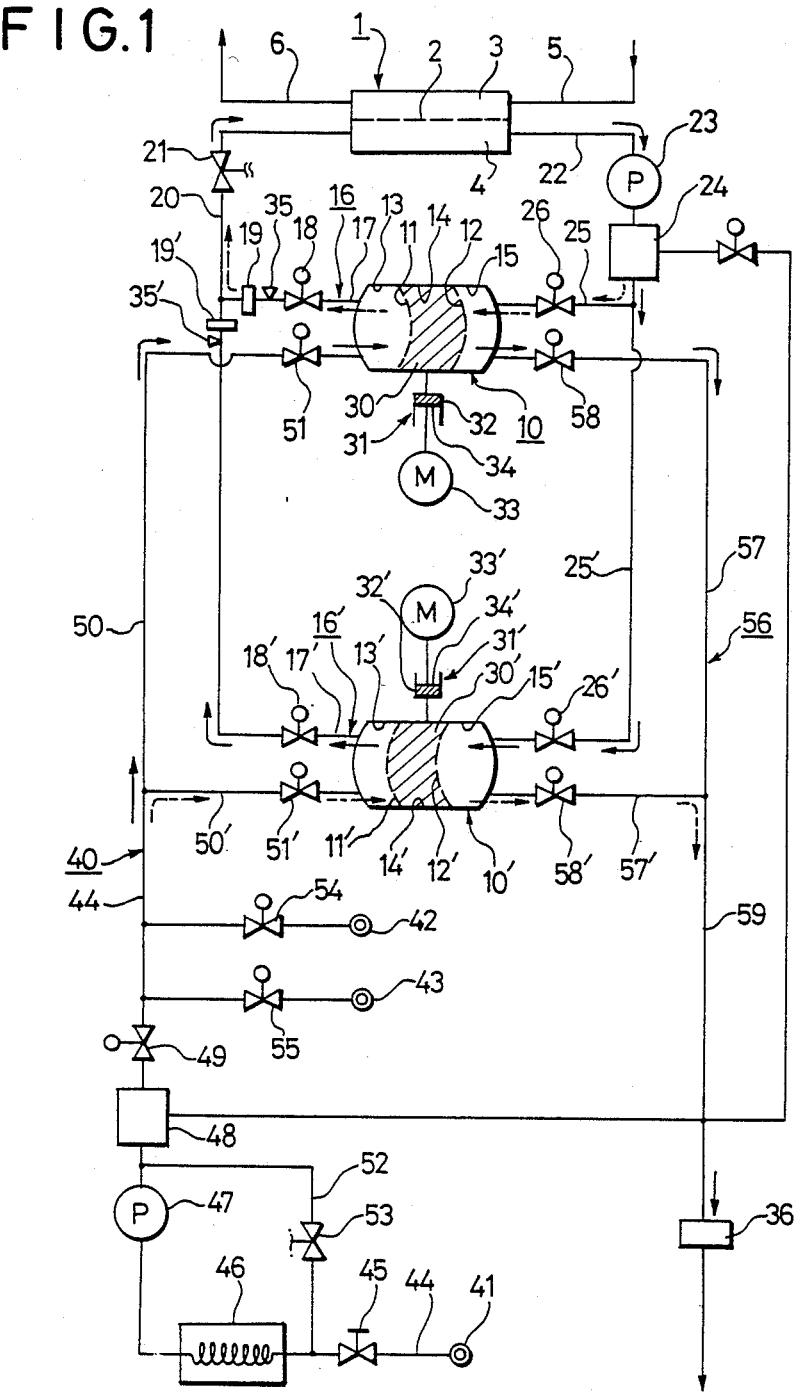
FIG. 1 is a diagrammatic view of one embodiment of the invention.

Referring to the drawings, several embodiments of the invention will now be described. Referring to FIG. 1, a dialyzer 1 includes a semi-permeable diaphragm 2 which divides it into a chamber 3 for liquid to be processed and a dialysate chamber 4. Processed liquid represents blood which is introduced into the processed liquid chamber 3 through a feed passage 5 and is externally drained out through a discharge passage 6.

In this embodiment, a pair of first and second dialysate containers 10, 10' are juxtaposed for alternately supplying the fresh dialysate to and displacing used dialysate from the dialyzer 1, thus enabling a dialysis operation. It is to be noted that the first and the second container 10, 10' are constructed in substantially the same manner, and hence the construction of only the first container 10 will be described, with corresponding parts of the second container 10' being denoted by like numerals as applied to the first container 10 with "prime".

The interior of the first container 10 is divided by a pair of movable diaphragms 11, 12 into three chambers, including a first feed chamber 13, a first variable volume chamber 14 and a first recovery chamber 15. Fresh dialysate which is prepared in the first feed chamber 13 which is located on one side of the container 10 is supplied through a first closed line 16 to the dialysate chamber 4 of the dialyzer 1, and used dialysate is recovered from the dialyzer into the first recovery chamber 15 which is located on the other side of the container 10. It is to be understood that the diaphragms 11 and 12 need not be completely separate, but may be partly connected together in an integral manner.

The first closed line 16 establishes a communication between the first feed chamber 13 and the dialysate chamber 14 through a first feed passage 17, a first feed valve 18, a filter 19, a common feed passage 20 and a constant flow rate valve 21, and also establishes a communication between the dialyzer and the first recovery chamber 15 through a common recovery passage 22, a pump 23, a deaerator 24, a first recovery passage 25 and a first recovery valve 26. The first variable volume chamber 14 which is defined centrally within the first container 10 has a quantity of liquid 30 such as silicone oil, for example, sealed therein such that whenever one of the diaphragms 11, has moved, the other diaphragm 12 is allowed to be displaced in following relationship with the diaphragm 11 through the liquid 30 interposed therebetween. In this manner, the liquid 30 constitutes interlock means which provides a linkage between both diaphragms 11 and 12 in the present embodiment.

A cylinder unit 31 includes a cylinder chamber 32 which communicates with the first variable volume chamber 14, and also includes a piston 34 which is driven by a servo motor 33 to move back and forth, thus permitting the volume of the first variable volume chamber 14 to be adjusted. The cylinder unit 31 is designed to exercise a greater degree of control over the volume of the chamber 14 when the diaphragms 11 and 12 are driven to the right and to exercise a lesser degree of control over the volume of the chamber 14 when the diaphragms are driven to the left.

As a consequence, it will be seen that a variation in the volume of the first recovery chamber 15 is greater than a variation in the volume of the first feed chamber 13 by an amount which is equal to a variation in the volume of the chamber 14 which is effected by means of the cylinder unit 31. This allows a greater amount of used dialysate, which exceeds the amount of fresh dialysate supplied to the dialyzer 1 from the first feed chamber 13 by an amount corresponding to the variation in the volume of the chamber 14, to be recovered into the first recovery chamber 15, with such variation in the volume of the chamber 14 coinciding with the amount of ultrafiltration by the dialyzer 1.

The filter 19 disposed in the first feed passage 17 permits a flow of the dialysate therethrough, but prevents a flow of the liquid 30 therethrough, thus preventing the liquid 30, which may leak into the first feed chamber 13 as a result of failure of the diaphragm 11, from being supplied to the dialyzer 1.

Detecting means 35 for detecting the liquid 30, such as a photo-tube 35 where a colored silicone oil is employed as a liquid 30, for example, is located upstream of the filter 19, permitting a breakdown of the diaphragm 11 to be detected whenever the dialysate becomes colored by contamination by the silicone oil. On the other hand, a breakdown of the diaphragm 12 can be detected by a blood leakage sensor 36, to be described later, which is capable of detecting the presence of a silicone oil.

A filter 19' corresponding to the filter 19 is disposed in a second closed line 16' associated with the second dialysate container 10' to permit a breakdown of the diaphragm 11' of the second container 10' to be detected, but a single filter may be disposed in the common feed passage 20 to simplify the arrangement.

Any suitable arrangement may be used to provide the detecting means 35 in consideration of the variety of the liquid 30 being used. As another example for the detecting means when the silicone oil is used as the liquid 30, part of or the entire second feed passage 17, located upstream of the filter 19, may comprise a transparent tube, allowing a visual recognition of a colored condition caused by the presence of the colored silicone oil.

A feed line 40 operates to feed fresh dialysate alternately to the first feed chamber 13 of the first dialysate container 10 and to the first feed chamber 13' of the second dialysate container 10'. It comprises a source of supply of dilution water 41, a source of supply 42 of concentrated liquid (hereafter referred to as "A liquid") containing calcium and magnesium ions, and a source of supply of concentrated liquid (hereafter referred to as "B liquid") containing bicarbonates 43.

The source of supply of dilution water 41 communicates with the first feed chamber 13 through a common inlet passage 44, a manual valve 45, a heater 46, a pump 47, a deaerator 48, a solenoid operated dilution liquid open/close valve 49, a first inlet passage 50 and a first inlet valve 51. The source of supply 41 also communicates with the second feed chamber 13' through a similar path as mentioned above, and then branching from the first inlet passage 50 to a second inlet passage 50' and through a second inlet valve 51'.

A bypass path 52 is connected between the output of the pump 47 and the inlet of the heater 46, and a relief valve 53 is disposed in this path so that the dilution air may be allowed to circulate through the bypass passage 52 and the relief valve 53 when the discharge pressure of the pump 47 exceeds a preselected pressure associated with the relief valve 53 as when the solenoid valve 49 is closed while maintaining the pump 47 in operation.

The source of supplies 42, 43 of A and B liquids are connected to the common inlet passage 44 extending between the valve 49, and the branch point between the both inlet passages 50, 50' through solenoid operated A-liquid open/close valve 54 and B-liquid open/close valve 55, respectively.

A waste line 56 which is used to drain out used dialysate from the first recovery chamber 15 comprises a first waste passage 57 connected to the first recovery chamber 15, a first waste valve 58 disposed therein, a common waste passage 59 and through the blood leakage sensor 36. It will be obvious that the waste line 56 also includes a second waste passage 57' connected to the second recovery chamber 15' and a second waste valve 58' disposed therein.

It is to be understood that the opening or closing of the solenoid operated valves as well as the rotation of the servo motors 33, 33' are controlled by a controller including a microcomputer, not shown.

Referring to a series of timing charts shown in FIG. 2, the operation of the dialysis system mentioned above will be described.

Figure 2:
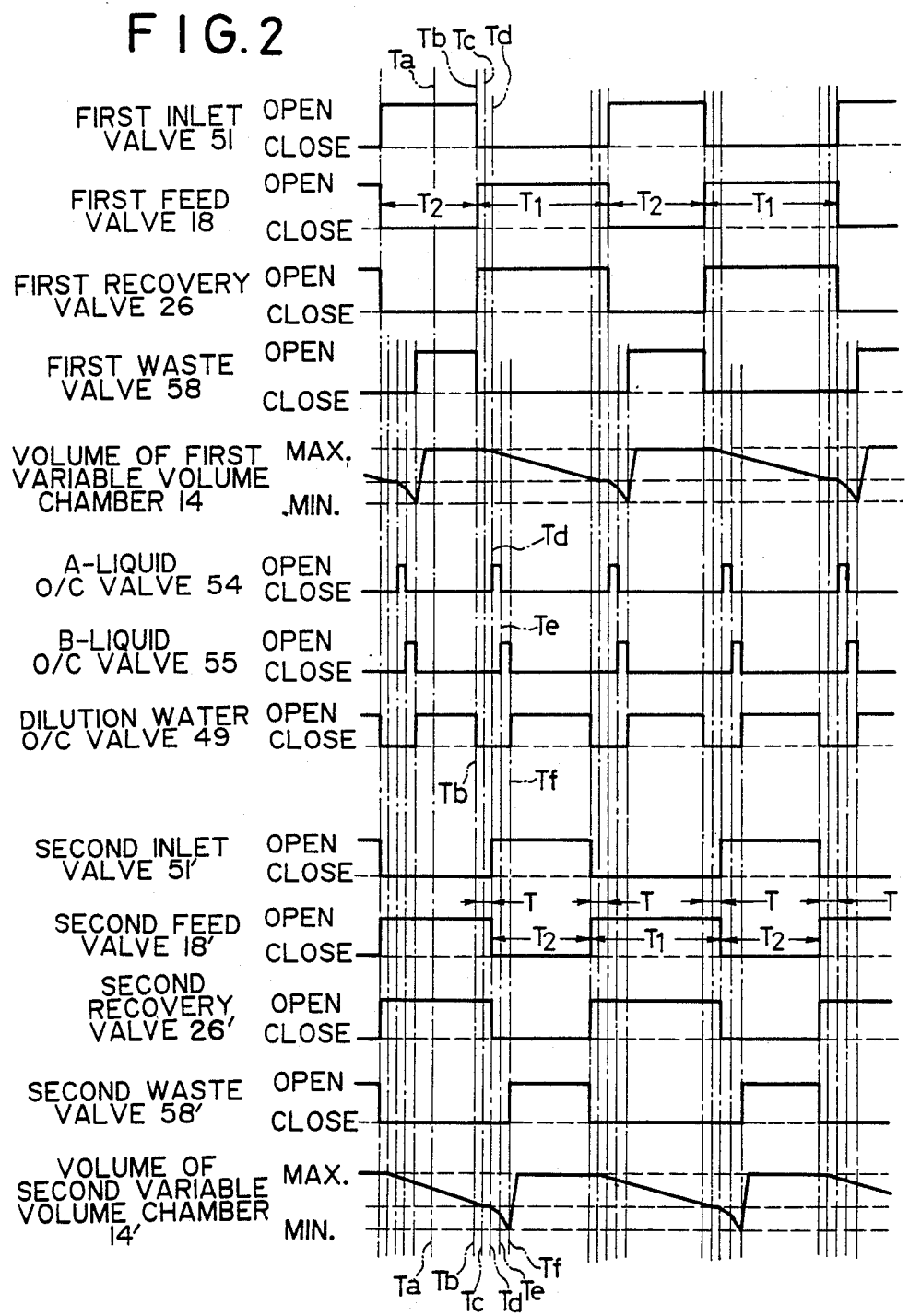
FIG. 2 is a series of timing charts which illustrate the operation of the embodiment shown in FIG. 1.

In the described embodiment, at time Ta shown in FIG. 2, the first feed valve 18 and the first recovery valve 26 are closed while the first inlet valve 51 and the first waste valve 58 are open in the first closed line 16. By contrast, the second feed valve 18' and the second recovery valve 26' are open while the second inlet valve 51' and the second waste valve 58 ' are closed in the second closed line 16', in opposite manner from the first closed line 16. Accordingly, under this condition, the second closed line 16' is connected to the dialysate chamber 4 of the dialyzer 1 while the first closed line 16 has its communication with the dialysate chamber 4 interrupted.

Under the condition mentioned above, a given quantity of A liquid and B liquid are already introduced into the first chamber 13, and A liquid open/close valve 54 and the B liquid open/close valve 55 are closed. In addition, the dilution liquid open/close valve 49 is open to permit dilution liquid to be introduced into the first feed chamber 13, thus allowing fresh dialysate to be prepared by mixing within the first feed chamber 13. As the dilution liquid is introduced into the first feed chamber 13, the diaphragms 11 and 12 move integrally, whereby the volume of the first recovery chamber 15 reduces, causing the used dialysate to be externally discharged through the waste passage 59 therefrom.

On the other hand, fresh dialysate present within the second feed chamber 13' is supplied to the dialysate chamber 4 of the dialyzer 1 with its flow rate being controlled to a given value by means of the constant flow rate valve 21. Used dialysate from the dialysate chamber 4 is recovered into the second recovery chamber 15'. At this time, the cylinder unit 31 operates to reduce the volume of the second variable volume chamber 14' at a given create gradually, whereby an amount of used dialysate which is greater than the amount of fresh dialysate that is supplied from the second feed chamber 13' into the dialysate chamber 4 is gradually recovered into the second recovery chamber 15', with the difference representing the amount of ultrafiltration in the dialyzer 1.

Fresh dialysate is supplied to the dialysate chamber 4 from each of the feed chambers 13, 13' in the first and the second closed lines 16 and 16', respectively, during a supply time interval $T_1$, during which the feed valves 18, 18' and the recovery valves 26, 26' are maintained open. The duration of the supply interval $T_1$ is previously chosen to be a suitable value on the basis of the capacity of each feed chamber 13, 13' and the flow rate which is controlled by the constant flow rate valve 21 so that the fresh supply of dialysate present within the feed chamber cannot be completely exhausted within such interval.

On the other hand, the fresh dialysate is introduced into the feed chambers 13, 13' through the inlet passage 44 over an introduction time interval $T_2$, during which the inlet valves 51, 51' and the waste valves 58, 58' are maintained open. The introduction interval $T_2$ has a duration less than that of the supply interval $T_1$. In this manner, each of the first and the second feed valve 18, 18' are maintained open in an overlapped manner during a given time interval T which is determined by the both intervals $T_1$ and $T_2$ as a difference therebetween.

At time Tb shown in FIG. 2 when the given introduction interval $T_2$ has passed within the first closed line 16, fresh dialysate has been prepared already within the first feed chamber 13, and the diaphragms 11 and 12 are located at their rightmost end. Under this condition, since the first feed chamber 13 is full, the dilution water fed from the pump 47 circulates through the bypass passage 52 and the relief valve 53 back to the pump 47, and the first variable volume chamber 14 is at its maximum volume.

At time Tb, the dilution water open/close valve 49 is closed and simultaneously the various valves within the first closed line 16 are switched over in a synchronous manner. Thus, the first feed valve 18 and the first recovery valve 26 are opened while the inlet valve 51 and the first waste valve 58 are closed. Consequently, the first closed line 16 is also connected to the dialysate chamber 4 of the dialyzer 1 simultaneously with the second closed line 16', and thus the fresh dialysate from both the first and the second feed chamber 13, 13' continues to be supplied to the dialysate chamber within the dialyzer 1 while recovering used dialysate from the chamber 4 into both the first and the second recovery chamber 15, 15'. It should be understood that, the flow rate of the fresh dialysate which is being supplied to the dialysate chamber 4 is maintained constant by the valve 21.

When the first and the second closed lines 16 and 16' are concurrently connected to the dialysate chamber 4 to maintain a continued supply of fresh dialysate thereto, at time Tc shown in FIG. 2, the second variable volume chamber 14' of the second closed line 16' which has initially been connected to the dialysate chamber 4 ceases to reduce its volume, and simultaneously the first variable volume chamber 14 of the first closed line 16 which is subsequently connected to the dialysate chamber 4 begins to decrease its volume at a given rate gradually.

By continuously reducing the volume of the first and the second variable volume chamber 14, 14' at a given rate, combined with the continuing supply of fresh dialysate to the dialysate chamber 4 from the both closed lines 16, 16', the ultrafiltration can be continued at a given rate.

At time Td shown in FIG. 2 when the supply time interval $T_1$ for the second closed line 16' passes, the second feed valve 18' and the second recovery 26' therein are closed, and the second inlet valve 51' is opened while the second waste valve 58' remains closed. As a result of closure of the second feed valve 18' and the second recovery valve 26', a communication between the second closed line 16' and the dialysate chamber 4 is interrupted, whereby the fresh dialysate continues to be supplied to the dialysate chamber 4 only from the first closed line 16.

At time Td when the second inlet valve 51' is opened while the second waste valve 58' remains closed, the A liquid open/close valve 54 is initially opened, and the second variable volume chamber 14' has it volume reduced to a predetermined value. Thereupon, since the diaphragm 12' is not allowed to move as a result of the closure of the second waste valve 58', only the diaphragm 11' is operated to increase the volume of the second reed chamber 13', enabling a given quantity of A liquid to be drawn into the second feed chamber 13' from the source of supply 42 through the A liquid open/close valve 54.

When the given quantity of A liquid has been introduced into the second feed chamber 13', the valve 54 is closed while the B liquid open/close valve 55 is opened at time Te, whereupon the second variable volume chamber 14' has its volume reduced to a predetermined value. In this manner, a given quantity of B liquid is allowed to be drawn into the second feed chamber 13' from the source of supply 43 through the B liquid open/close valve 55, generally in the similar manner as mentioned above.

After the given quantity of A liquid and B liquid has been introduced into the second feed chamber 13', the valve 55 is closed while the dilution water open/close valve 49 is opened at time Tf. The second waste valve 58' is also opened.

Then the pump 47 operates to pump the dilution liquid into the second feed chamber 13' through the valve 49, whereby the diaphragms 11 and 12 are driven integrally to the right, causing the used dialysate to be externally drained out from the second recovery chamber 15'. In the meantime, the cylinder unit 31' operates to return the volume of the second variable volume chamber 14' rapidly to its maximum volume from its reduced volume condition mentioned above.

It will be recognized that the condition now reached by the first and the second closed lines 16, 16' is opposite from that which prevails at time Ta. Thus, the described operation of the respective closed lines 16, 16' is subsequently repeated. Since the respective closed lines 16, 16' are connected alternately to the dialysate chamber 4 of the dialyzer 1 with a given length of time interval T overlapped therebetween, it is assured that fresh dialysate is continuously supplied to the dialysate chamber 4 in a stabilized manner, thus enabling a continuous, smooth ultrafiltration.

Where fresh dialysate is supplied to the feed chambers 13, 13' under a given pressure, a constant flow rate valve 21 may comprise a throttle valve such as needle valve.

In the described embodiment, when fresh dialysate is prepared by mixture, the A liquid, the B liquid and the dilution liquid have been sequentially introduced and mixed in this order, but the order of introduction is not limited thereto. By way of example, the dilution liquid may initially be supplied up to its half its predetermined quantity, followed by a sequential introduction of given quantities of A and B liquids as mentioned, and finally followed by the introduction of the rest of dilution liquid into the feed chamber 13, 13' until the latter become filled.

A pair of sources of supply 42 and 43 are utilized in the described embodiment to provide two kinds of concentrated liquids A and B. However, it should be understood that the source of supply of concentrated liquid or liquids may be one or three or greater depending on the kind of the dialysate being used.

On the other hand, while fresh dialysate is prepared by mixture within each of the feed chambers 13, 13' in the described embodiment, fresh dialysate which is externally prepared may be fed into the respective feed chambers 13, 13'. In this instance, because a variation in the volume of the variable volume chambers 14, 14' occur in a symmetrical manner, thus, one increasing while the other is decreasing, the both variable volume chambers 14, 14' may be connected together through a communication passage with a pump disposed therein which feeds the liquid 30 from one of the variable volume chambers to the other or vice versa.

It is to be understood that the overlapped operation between the both closed lines over the time interval T is possible either if the fresh dialysate is prepared within the respective feed chambers 13, 13' or if the fresh dialysate which is externally prepared is fed to the respective feed chambers 13, 13'.

Figure 3:
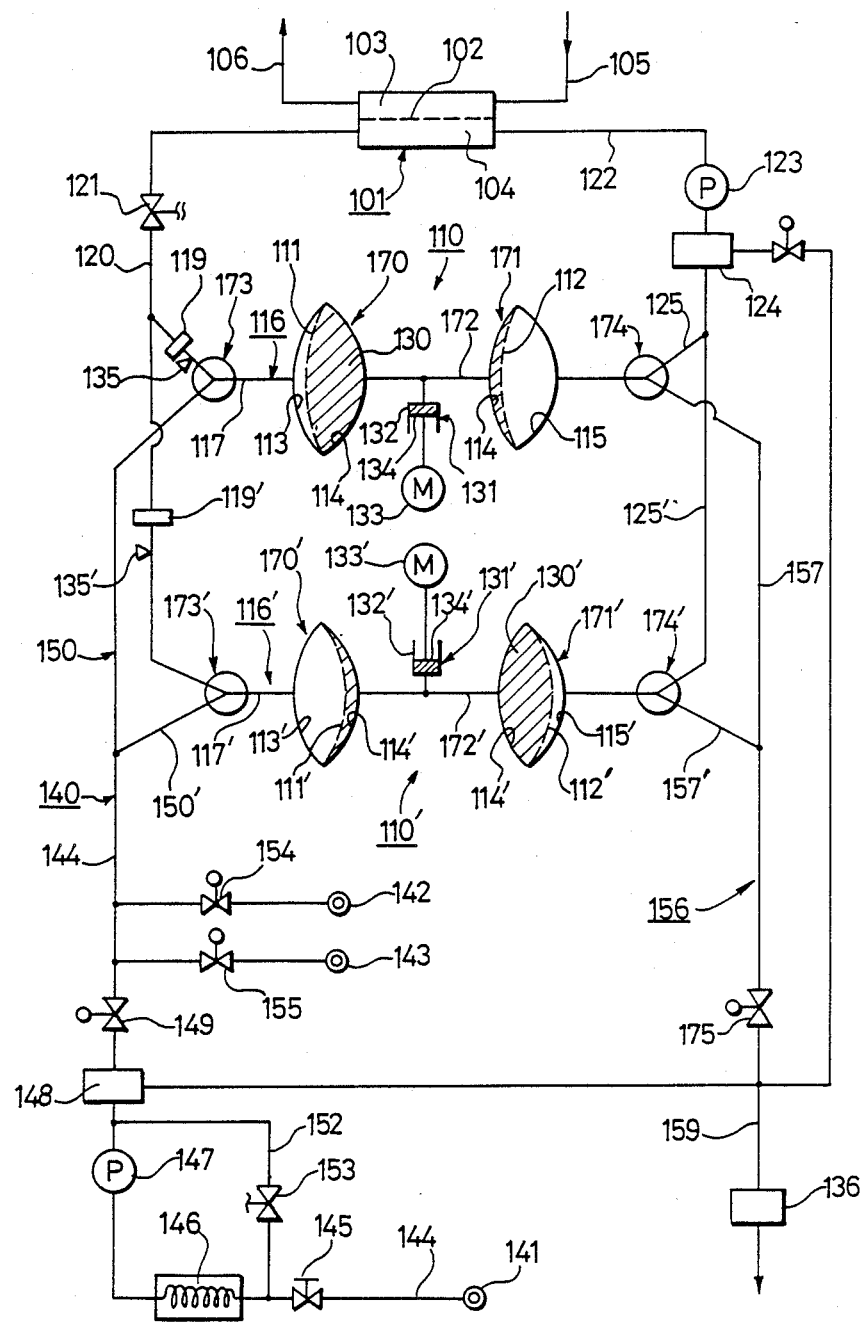
FIG. 3 is a diagrammatic view of another embodiment of the invention.

FIG. 3 shows another embodiment of the invention including a first dialysate container 110 which is equivalent to the first dialysate container of the previous embodiment and divided into separate container sections 170, 171 at a point intermediate the diaphragms 111 and 112. Each of the containers 170, 171 is formed with a variable volume chamber 114, which is connected together through a piping 172 which is in turn connected to a cylinder chamber 132 of a cylinder unit 131. A second dialysate container 110' is constructed in a similar manner, and part thereof which corresponds to those of the first container 110 are designated by like reference numerals with a prime.

In this embodiment, each of feed chambers 113, 113' is connected to a dialysate chamber 104 of a dialyzer 101 or a feed line 140 for fresh dialysate in a switched manner through three way valves 173, 173' which are substituted for the feed valves 18, 18' and inlet valves 51, 51'. Similarly, three way valves 174, 174' are substituted for the recovery valves 26, 26' and the waste valves 58, 58'. A solenoid operated open/close valve 175 is disposed in a waste line 156 in order to introduce the A liquid and the B liquid into the respective feed chambers 113, 113'.

In other respects, the arrangement is substantially similar to the previous embodiment, and accordingly, corresponding parts are designated by like reference numerals as used before to which 100 are added. It will be apparent that a similar effect can be achieved as that achieved by the first embodiment.

FIG. 4 schematically shows a dialysate container of a further embodiment. In this embodiment, a dialysate container 210 includes a cylinder unit 280 having a piston 281 connected to a piston rod 282, which is connected to a rockable arm 284, which is rockable about a fulcrum 283, at a joint 285. The rockable arm 284 is also connected at a joint 289 to a piston rod 288 connected to a piston 287 associated with another cylinder unit 286.

The joint 289 is located further from the fulcrum 283 than the other joint 285, whereby the cylinder units 280 and 286 experience different piston strokes as the arm 284 rocks. In this manner, a variation in the volume of a recovery chamber 215 defined within the cylinder 286 which is caused by the piston 287 serving as a movable diaphragm is made greater than a variation in the volume of a feed chamber 213 defined within the cylinder unit 280 which is caused by the piston 281 also serving as a movable diaphragm.

A cylinder unit 290 is disposed intermediately the piston rod 282 associated with the feed chamber 213 to provide a two step operation. When the rockable arm 284 is fixed in position by a stop 291, the operation of the cylinder unit 290 to its first step causes the A liquid to be drawn to the feed chamber 213, and subsequently when the cylinder unit 290 is operated to its second step, the B liquid is withdrawn into the chamber 213. At least one of the joints 285, 289 is located to be movable lengthwise along the rockable arm 284, thus enabling the difference in the variations of volumes to be adjusted.

The arrangement shown in FIG. 4 may be used as a dialysate container in each embodiment described above with similar effect.

While the invention has been shown and described above in connection with several embodiments thereof, it should be understood that a number of changes, modifications and substitutions will readily occur to one skilled in the art without departing from the spirit and scope of the invention defined by the appended claims.

What is claimed is:

1. A dialysis system, comprising: container means for temporarily storing fresh and used dialysate, said container means having therein a pair of separate movable diaphragms which define therein a feed chamber and a recovery chamber, each of variable volume, a dialyzer having an inlet which is connected to said feed chamber and also having an outlet which is connected to said recovery chamber, whereby a closed line is defined by the feed chamber, the dialyzer and the recovery chamber, fresh dialysate which is introduced into the feed chamber being supplied to the dialyzer in response to a reduction in the volume of the feed chamber while used dialysate is simultaneously recovered from the dialyzer into the recovery chamber in response to an increase in the volume of the recovery chamber;

interlock means for mechanically coupling said pair of movable diaphragms for movement together in said container means such that the volume of the recovery chamber changes simultaneously with a correspondingly equal and opposite change in the volume of the feed chamber, further comprising control means associated with said interlock means and cooperable therewith for alternatively effecting relative movement of said movable diaphragms and causing the volume of the recovery chamber and the volume of the feed chamber to simultaneously change by respectively different amounts.

2. A dialysis system according to claim 1 in which said movable diaphragms are disposed in said container means, a variable volume chamber being defined intermediately between the diaphragms in said container means, the feed chamber being defined by one of the diaphragms on one side of the variable volume chamber and the recovery chamber being defined by the other of the diaphragms on the other side of the variable volume chamber, the interlock means comprising liquid which fills the variable volume chamber, the control means including means for causing a variation in the volume of the variable volume chamber.

3. A dialysis system according to claim 2 in which the control means comprises a cylinder unit including a cylinder chamber which communicates with the variable volume chamber, means for changing the internal volume of said cylinder chamber, and a servo motor for operating said volume changing means to control the internal volume of the cylinder chamber.

4. A dialysis system according to claim 1, wherein said container means includes first and second containers, and wherein said movable diaphragms are first and second movable diaphragms respectively disposed in said first and second containers, said first diaphragm serving to define in said first container the feed chamber on one side thereof and a first variable volume chamber on the other side thereof, and said second diaphragm serving to define in said second container the recovery chamber on one side thereof and a second variable volume chamber on the other side thereof, the first and the second variable volume chambers being in communication with each other and being filled with a liquid which operates as the interlock means, the control means including means for causing a change in the volume of the first and second variable volume chambers.

5. A dialysis system according to claim 4 in which the control means comprises a cylinder unit including a cylinder chamber which communicates with the variable volume chambers, means for changing the internal volume of said cylinder chamber, and a servo motor for operating said volume changing means to control the internal volume of the cylinder chamber.

6. A dialysis system according to claim 1, wherein said container means includes a first cylinder unit in which the feed chamber is defined, and a second cylinder unit in which the recovery chamber is defined, wherein said pair of movable diaphragms are first and second pistons respectively slidably disposed in said first and second cylinder units and defining therein said feed chamber and said recovery chamber, wherein the interlock means includes a pivotally supported rockable arm, a first piston rod connected between the first piston and the rockable arm, and a second piston rod connected between the second piston and the rockable arm, and wherein the control means includes means for displacing the connection of at least one of said piston rods with the rockable arm lengthwise of the arm.

7. A dialysis system according to claim 1, further comprising a feed line communicating with said feed chamber for feeding fresh dialysate into the feed chamber, the feed line comprising a source of concentrated liquid which is connected to at least the feed chamber through a first open/close valve, and a source of dilution water connected to the feed chamber through a second open/close valve, the movable diaphragm which defines the feed chamber being driven to increase the volume of the feed chamber whenever fresh dialysate is introduced into the feed chamber, and further including means for alternately opening the first and the second open/close valves to admit a given quantity of concentrated liquid and dilution water into the feed chamber sequentially, thereby allowing fresh dialysate to be prepared within the feed chamber by mixture.

8. A dialysis system according to claim 1, further comprising a feed line communicating with said feed chamber for feeding fresh dialysate into the feed chamber, the feed line comprising a source of concentrated liquid containing calcium and magnesium ions and connected to the feed chamber through a first open/close valve, a source of concentrated liquid containing bicarbonate and connected to the feed chamber through a second open/close valve, and a source of dilution water connected to the feed chamber through a third open/close valve, the arrangement being such that when fresh dialysate is introduced into the feed chamber, the movable diaphragm which defines the feed chamber is driven to increase the volume of the feed chamber, and further including means for sequentially opening the first, the second and the third open/close valves in a given sequence, allowing given quantities of the respective concentrated liquid and dilution water to be sequentially introduced into the feed chamber and mixed therein to prepare fresh dialysate.

9. A dialysis system according to claim 1 in which said container means comprise first and second container for temporarily sorting fresh and used dialysate, said first container having a first said feed chamber and a first said recovery chamber, said second container having a second said feed chamber and a second said recovery chamber, first and second ones of said closed lines respectively connecting said dialyzer with said first and second containers, said first and second closed lines including means defining selectively openable and closable first and second feed passages respectively communicating said first and second feed chambers with the dialyzer for supplying fresh dialysate respectively from said first and second feed chambers to the dialyzer, and further including means defining selectively openable and closable first and second recovery passages respectively communicating said first and second recovery chambers with the dialyzer for recovering sued dialysate from the dialyzer respectively into said first and second recovery chambers, a feed line for feeding fresh dialysate into said feed chambers, a waste line for draining used dialysate from said recovery chambers, and means for opening said first feed passage and said first recovery passage and for thereafter opening said second feed passage and said second recovery passage so as to alternatingly sue said first and second containers to supply fresh dialysate to and recover used dialysate from the dialyer, and further including means for keeping said first feed passage and said first recovery passage open until after said second feed passage and said second recovery passage have been opened, so that fresh dialysate is continuously supplied to the dialyers, said first feed and recovery passages being held open for a supply time period.

10. The dialysis system according to claim 9, including means for connecting said feed chambers and said recovery chambers respectively to said feed line and said waste line, and further including means for holding said feed chambers and said recovery chambers connnected to said feed line and said waste line for an introduction time period which is less than said supply time period.

11. A dialysis system comprising: means defining a feed chamber and including a movable diaphragm, means defining a recovery chamber and including a separate movable diaphragm, a dialyzer having an inlet which is connected to said feed chamber and also having an outlet which is connected to said recovery chamber, whereby a closed line is defined by the feed chamber and the dialyzer and the recovery chamber, fresh dialysate which is introduced into the feed chamber being supplied to the dialyzer in response to a reduction in the volume of the feed chamber while sued dialysate is simultaneously recovered from the dialyzer into the recovery chamber in response to an increase in the volume of the recovery chamber;

interlock means for linking said movable diaphragms together to increase or decrease the volume of the recovery chamber respectively in response to a decrease or increase in the volume of the feed chamber, further comprising control means associated with said interlock means and operable to control a difference between a variation in the volume of the recovery chamber and a variation in the volume of the feed chamber;

means including the first mentioned movable diaphragm for defining a first variable volume chamber on the other side of said first mentioned diaphragm from said feed chamber, and means including said separate movable diaphragm defining a second variable volume chamber on the other side of said separate diaphragm from said recovery chamber, the first and second variable volume chambers being in communication with each other and being filled with a liquid which operates as the interlock means;

said dialysis system further comprising a feed passage which communicates the feed chamber with the dialyzer, and a filter disposed in the feed passage for permitting a flow of a fresh dialysate and for blocking a flow of the liquid which fills the variable volume chambers.

12. A dialysis system according to claim 11, further comprising detecting means located in the feed passage upstream of the filter for detecting the presence or absence of the liquid which fills the variable volume chambers.

13. A dialysis system comprising: means defining a feed chamber and including a movable diaphragm, means defining a recovery chamber and including a separate movable diaphragm, a dialyzer having an inlet which is connected to said feed chamber and also having an outlet which is connected to said recovery chamber, whereby a closed line is defined by the feed chamber and the dialyzer and the recovery chamber, fresh dialysate which is introduced into the feed chamber being supplied to the finalize in response to a reduction in the volume of the feed chamber while used dialysate is simultaneously recovered from the dialyzer into the recovery chamber in response to an increase in the volume of the recovery chamber;

interlock means for linking said movable diaphragms together to increase or decrease the volume of the recovery chamber respectively in response to a decrease or increase in the volume of the feed chamber, further comprising control means associated with said interlock means and operable to control a difference between a variation in the volume of the recovery chamber and a variation in the volume of the feed chamber;

means defining a variable volume chamber intermediately between the diaphragms, the interlock means comprising liquid which fills the variable volume chamber;

said dialysis system further comprising a feed passage which communicates the feed chamber with the dialyzer, and a filter disposed in the feed passage for permitting a flow of a fresh dialysate and for blocking a flow of the liquid which fills the variable volume chamber.

14. A dialysis system according to claim 13, further comprising detecting means located in the feed passage upstream of the filter for detecting the presence or absence of the liquid which fills the variable volume chamber.

* * * * *

UNITED STATES PATENT AND TRADEMARK OFFICE
CERTIFICATE OF CORRECTION

PATENT NO. : 4,935,125
DATED : June 19, 1990
INVENTOR(S) : Kazuo ERA et al.

It is certified that error appears in the above-identified patent and that said Letters Patent is hereby corrected as shown below:

Col. 11, lines 66-67; change "first and second container for" to ---first and second containers for---.

Col. 11, line 67; change "temporarily sorting" to ---temporarily storing---.

Col. 12, line 15; change "recovering sued dialysate" to ---recovering used dialysate---.

Col. 12, line 22; change "alternatingly sue said first" to ---alternatingly use said first---.

Col. 12, line 24; change "from the dialyer" to ---from the dialyzer---.

Col. 12, line 49; change "while sued dialysate" to ---while used dialysate---.

Col. 13, line 25; change "supplied to the finalize" to ---supplied to the dialyzer---.

Signed and Sealed this

Seventeenth Day of December, 1991

Attest:

HARRY F. MANBECK, JR.

*Attesting Officer*  *Commissioner of Patents and Trademarks*